United States Patent
Dalvi et al.

(10) Patent No.: US 10,653,704 B2
(45) Date of Patent: May 19, 2020

(54) INHALABLE FORMULATION

(71) Applicant: Teva Branded Pharmaceutical Products R&D, Inc., Frazer, PA (US)

(72) Inventors: Mukul Dalvi, Weston, FL (US); Jacquelyn McCabe, Davie, FL (US)

(73) Assignee: Teva Branded Pharmaceutical Products R&D, Inc., Frazer, PA (US)

( * ) Notice: Subject to any disclaimer, the term of this patent is extended or adjusted under 35 U.S.C. 154(b) by 0 days.

(21) Appl. No.: 15/519,460

(22) PCT Filed: Oct. 16, 2015

(86) PCT No.: PCT/US2015/055916
§ 371 (c)(1),
(2) Date: Apr. 14, 2017

(87) PCT Pub. No.: WO2016/061445
PCT Pub. Date: Apr. 21, 2016

(65) Prior Publication Data
US 2017/0239269 A1 Aug. 24, 2017

Related U.S. Application Data

(60) Provisional application No. 62/064,684, filed on Oct. 16, 2014.

(51) Int. Cl.
*A61K 31/56* (2006.01)
*A61K 9/12* (2006.01)
*A61K 9/00* (2006.01)

(52) U.S. Cl.
CPC .............. *A61K 31/56* (2013.01); *A61K 9/008* (2013.01); *A61K 9/0075* (2013.01); *A61K 9/124* (2013.01)

(58) Field of Classification Search
CPC ...... A61K 31/56; A61K 9/0075; A61K 9/008; A61K 9/124
See application file for complete search history.

(56) References Cited

U.S. PATENT DOCUMENTS

| | | | |
|---|---|---|---|
| 7,163,672 B2 | 1/2007 | Buckton et al. | |
| 9,980,904 B2 * | 5/2018 | Dalvi | A61K 9/0073 |
| 2002/0122826 A1 | 9/2002 | Lizio et al. | |
| 2002/0176824 A1 | 11/2002 | Riebe et al. | |
| 2005/0152845 A1 * | 7/2005 | Biggadike | C07J 17/00 424/46 |
| 2007/0009445 A1 | 1/2007 | Eck | |

FOREIGN PATENT DOCUMENTS

WO 2014173987 A1 10/2014

OTHER PUBLICATIONS

International Search Report for International Application No. PCT/US2015/055916, 2 pages.
Written Opinion for International Application No. PCT/US2015/055916, 6 pages.
Ukrainian Office Action for Application No. a 2017 04603(MI-12828); dated May 4, 2019; 6 pages.
English translation of Ukrainian Office Action for Application No. a 2017 04603(MI-12828); dated May 4, 2019; 4 pages.
Japanese Patent Application No. 2014-519634; Notice of Reasons for Refusal; dated Jun. 26, 2019; 7 pages.
English translation of Japanese Patent Application No. 2014-519634; Notice of Reasons for Refusal; dated Jun. 26, 2019; 6 pages.
EP Office Action for EP 15787397; Annex to communication; dated Oct. 8, 2019; 1 page.
Eurasian Office Action for EA Patent Application No. 201790832; Sep. 26, 2019; 2 pages.
English translation of Eurasian Office Action for EA Patent Application No. 201790832; 1 page.
Office Action for Mexican Patent Application No. MX/a/2017/004765 dated Feb. 18, 2020.

* cited by examiner

*Primary Examiner* — Mina Haghighatian
(74) *Attorney, Agent, or Firm* — Morgan, Lewis & Bockius LLP

(57) ABSTRACT

This invention provides a process for preparing an inhalable active pharmaceutical ingredient comprising the steps of heating a suspension of an active pharmaceutical ingredient in a liquefied propellant in a vessel, evaporating the propellant and collecting the resultant powder.

14 Claims, 2 Drawing Sheets

INHALABLE FORMULATION

CROSS-REFERENCE TO RELATED APPLICATIONS

Figure 1:
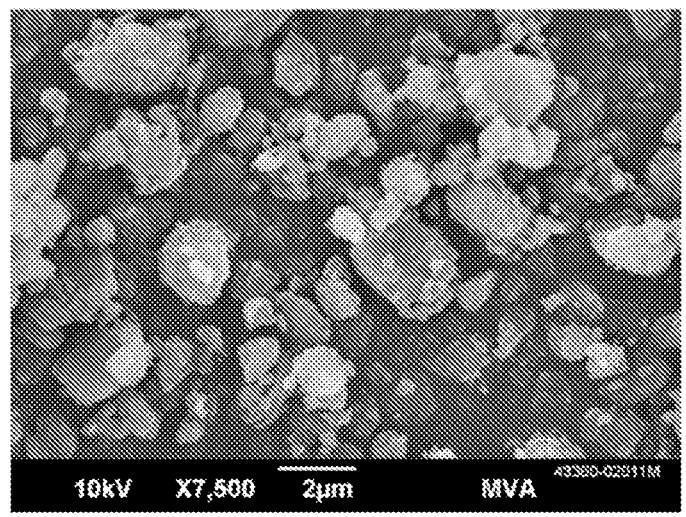
Figure 1:
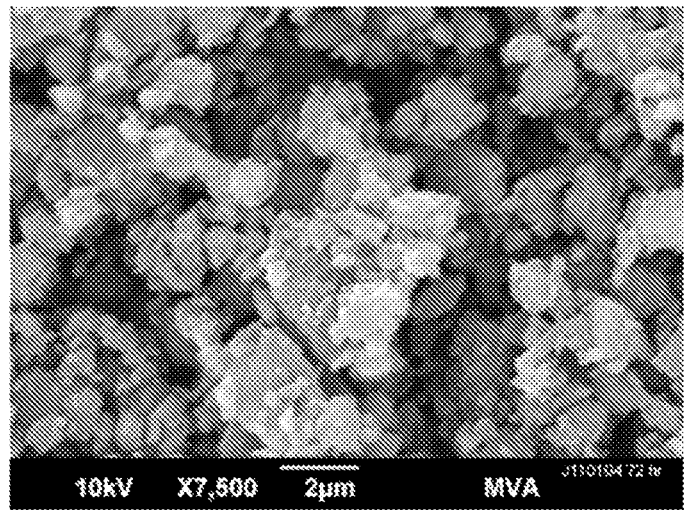

This application is a U.S. National Stage filing of International Patent Application No. PCT/US15/55916 filed Oct. 16, 2015, which claims priority to U.S. Provisional Application No. 62/064,684, filed Oct. 16, 2014, the entire disclosure of each is incorporated herein by reference in their entirety for all purposes.

FIELD OF THE INVENTION

This invention relates to a process for preparing an active pharmaceutical ingredient. More specifically, the invention relates to an inhalable formulation and particularly to a process for preparing an inhalable formulation with reduced amorphous content in the active pharmaceutical ingredient (API).

BACKGROUND OF THE RELATED ART

The present invention is directed to the provision of an inhalable formulation containing one or more APIs for the treatment of respiratory disorders such as asthma or COPD. A range of classes of medicaments have been developed to treat respiratory disorders and each class has differing targets and effects. A common feature of inhalable medicaments is that they must penetrate deep into the lung in order to reach their site of action.

To this end, the APIs are micronised, e.g. by jet milling, in order to obtain particles having the required size, typically a mass median aerodynamic diameter (MMAD) of 1-5 μm. However, the energy imparted to the particles of the API by the micronisation technique often leads to the introduction of amorphous character into the otherwise crystalline material of the API particles. Regions of amorphous character are generally regarded in the art as being undesirable, primarily because they have a tendency to absorb water leading to agglomeration of the API particles. This unpredictability detrimentally affects the particle size distribution (PSD) of the API which in turn affects the amount of fine particles of API reaching the lungs, quantified by the fine particle fraction (FPF), as determined using an impactor.

Various techniques have been proposed to remove these regions of amorphous character from micronised API particles. They typically involve recrystallising the amorphous region by exposing the micronised particles to a humid environment. See, for example, the discussion of this approach in Particulate Interactions in Dry Powder Formulations for Inhalation, X. M. Zeng et al., Taylor & Francis, London, 2000.

However, there remains a need in the art for alternative and improved approaches.

BRIEF SUMMARY OF THE INVENTION

Accordingly, the present invention provides a process for preparing an inhalable active pharmaceutical ingredient comprising the steps of heating a suspension of an active pharmaceutical ingredient in a liquefied propellant in a vessel, evaporating the propellant and collecting the resultant powder.

BRIEF DESCRIPTION OF THE DRAWINGS

FIGS. 1 and 2 show scanning electron microscope images of fluticasone propionate, pre-conditioning (the first image in each Figure) and post-conditioning (the second image in each Figure).

DETAILED DESCRIPTION OF CERTAIN EMBODIMENTS OF THE INVENTION

The processes described herein would be applicable to preparing any active pharmaceutical ingredient (API) where there is a need to reduce the amorphous content in the crystalline API, for example to improve chemical stability.

The present invention provides a process for preparing the inhalation product. It has been found that performing the conditioning step where the API is suspended in a liquefied propellant leads to a surprisingly rapid conditioning and a more stable PSD. This would be measured by measuring the stability of the API in the finished product, i.e. Aerodynamic Particle Size Distribution (APSD), as would be understood by a person of skill in the art.

There may be one or more APIs present during the conditioning step.

The API is preferably a bronchodilator and/or an inhaled glucocorticosteroid. Bronchodilators are employed to dilate the bronchi and bronchioles, decreasing resistance in the airways, thereby increasing the airflow to the lungs. Bronchodilators may be short-acting or long-acting. Short-acting bronchodilators provide a rapid relief from acute bronchoconstriction, whereas long-acting bronchodilators help control and prevent longer-term symptoms. Different classes of bronchodilators target different receptors in the airways. Two commonly used classes are $\beta_2$-agonists and anticholinergics.

$\beta_2$-Adrenergic agonists (or "$\beta_2$-agonists") act upon the $\beta_2$-adrenoceptors which induces smooth muscle relaxation, resulting in dilation of the bronchial passages. Examples of long-acting $\beta_2$-agonists (LABAs) include formoterol (fumarate), salmeterol (xinafoate), indacaterol (maleate), carmoterol (hydrochloride) and vilanterol (trifenatate). Examples of short-acting $\beta_2$-agonists (SABAs) include salbutamol (sulfate), terbutaline (sulfate), pirbuterol (acetate) and metaproterenol (sulfate).

Anticholinergics (also known as antimuscarinics) block the neurotransmitter acetylcholine by selectively blocking its receptor in nerve cells. On topical application, anticholinergics act predominantly on the $M_3$ muscarinic receptors located in the airways to produce smooth muscle relaxation, thus producing a bronchodilatory effect. Examples of long-acting muscarinic antagonists (LAMAs) include tiotropium (bromide), aclidinium (bromide), glycopyrronium (bromide), Umeclidinium (bromide), oxybutynin (hydrochloride or hydrobromide) and darifenacin (hydrobromide).

Another class of medicaments employed in the treatment of respiratory disorders are inhaled corticosteroids (ICSs). ICSs are steroid hormones used in the long-term control of respiratory disorders. They function by reducing the airway inflammation. Examples include budesonide, beclomethasone (dipropionate), mometasone (furoate) and fluticasone (propionate or furoate).

The API is preferably fluticasone, including pharmaceutically acceptable salts or solvates thereof.

The API is suspended in a liquefied propellant in a vessel. The vessel is preferably a drug-addition vessel. The liquefied propellant may be any propellant typically used for formulating pressurised metered dose inhaler (pMDI) formulations, such as a hydrofluoroalkane (HFA) propellant, e.g. HFA134a or HFA227, more preferably HFA134a.

The vessel preferably has a volume of 1-50 L. The API is preferably present at 1-30% by weight, based on the combined weight of the API and propellant. A batch size of 10 to 1000 g of API is preferred.

Heating is performed at a temperature of 30-50° C., more preferably at a temperature of 35-45° C., and most preferably at a temperature of 38-42° C. The heating step, in the presence of the propellant, is a conditioning step for the API, in order to reduce the amorphous content of the API, without affecting the PSD. Amorphous content may be determined by solution microcalorimetry.

The heating step is conducted for 6 hours to 5 days, more preferably 24-84 hours, most preferably 48-72 hours. In another embodiment, the heating step is conducted for 12-72 hours.

No other conditioning step is required. An initial conventional conditioning step may be applied, but it is not required. Preferably, the propellant-based heating step according to the present invention is the sole post-micronisation treatment step.

The propellant may be used as supplied, although water can be added. Water is not critical to the conditioning process but if water is added, then the water content of the propellant will typically be 0.01-3% by weight, based on the total weight of the propellant. Typically the water is no more than 0.05% in HFA 134a. Water content may be determined by Karl Fisher.

The external humidity of the heating step is less relevant. Preferably the relative humidity is less than 70% (i.e. 0-70%), more preferably 30-55% and most preferably 40-50%.

The suspension is preferably agitated during the heating step. The energy required to agitate the suspension may be provided externally or internally. Non-limiting examples of external energy sources include shaking plates, orbital shakers, vortex mixers, vibration shakers, wave shakers or rockers. Non-limiting examples of internal energy sources include an impeller, high-shear homogeniser, high-shear granulator, paddle blending, ribbon blending, drum blending or jet mixing.

The present invention also provides an inhalable active pharmaceutical ingredient obtainable by the present process. The product is distinguished, inter alia, by a smoother surface and more stable PSD over time.

The inhalable API may be formulated in any conventional manner, including as a dry powder formulation, a formulation for a pMDI, or an aqueous nebulisable formulation. In the latter two types of formulations, the API should preferably be in suspension in order to gain the benefit of the improved solid-state form provided by the present process.

A dry powder formulation typically contains the API and a coarse particulate carrier. The API needs to be in micronised form (typically a mass median aerodynamic diameter of 1-5 μm, more typically 2-4 μm). This size of particle is able to penetrate the lung on inhalation. However, such particles have a high surface energy and require a coarse carrier in order to be able to meter the formulation. Examples of particulate carriers include lactose, glucose, or sodium starch glycolate, preferably lactose and most preferably α-lactose monohydrate. The coarse carrier particles are of a size that, after inhalation, most of them remain in the inhaler or deposit in the mouth and upper airways. Accordingly, the carrier preferably has a volume mean diameter (VMD) of 40 microns or more, more preferably the carrier particles have a VMD of 50-250 microns. The particle size may be determined using laser light scattering with laser diffraction system, e.g. from Sympatec GmbH, Claasthal-Zellerfeld, Germany.

The formulation may be provided in an inhaler or a capsule.

The dry powder formulation may be presented in an inhaler, e.g. in the reservoir of a multi-dose dry powder inhaler (MDPI), for example inhalers sold under the brand name Spiromax®. Suitable MDPIs are also described in WO 92/10229 and WO 2011/054527. Such inhalers comprise a chassis, a dosing chamber, a mouthpiece and the medicament. The formulation may also be presented in a blister strip of unit doses within the inhaler, such as the dry powder nebuliser from MicroDose Therapeutx Inc. and the inhalers described in WO 2005/081833 and WO 2008/106616.

The dry powder formulation may alternatively be metered and filled into capsules, e.g. gelatin or hydroxypropyl methylcellulose capsules, such that the capsule contains a unit dose of active ingredient. When the dry powder is in a capsule containing a unit dose of active ingredient, the total amount of composition will depend on the size of the capsules and the characteristics of the inhalation device with which the capsules are being used.

A pMDI formulation contains the API and a liquefied HFA propellant. Examples of a propellant gas for preparing an aerosol formulation include HFA134a, HFA227 or mixtures thereof, most preferably HFA134a. In a preferred embodiment, the HFA propellant used in the formulation is the same propellant used in the process, and most preferably both the process and the formulation use HFA134a. The formulation may also contain co-solvents (e.g. ethanol and/or glycerol), surfactants (e.g. oleic acid) and/or an acid (e.g. citric acid). See EP 0 372 777, EP 0 616 525 and WO 98/05302 for further details of aerosol formulations. Pressured metered-dose inhalers of this type typically comprise a chassis, a mouthpiece and a canister comprising the medicament as described in the aforementioned documents.

A nebulisable formulation contains the API and water. The formulation may also contain co-solvents (e.g. ethanol) and/or an acid (e.g. citric acid).

The present invention will now be described with reference to the accompanying examples, which are not intended to be limiting.

Examples

Fluticasone propionate was conditioned in a drug-addition vessel. A 5% concentration of fluticasone propionate in HFA134a was treated at 40° C. for 48-72 h with a gentle rocking motion. HFA134a was vented and the remaining material was assessed in regard to its amorphous content. The results are set out in Table 1.

TABLE 1

Conditioning studies, untreated versus treated.

|  | Conditions | Particle size distribution (μm) by Malvern | | | Amorphous content (%) |
| --- | --- | --- | --- | --- | --- |
|  |  | D10 | D50 | D90 |  |
| Experiment 1 | Control (untreated) | 0.6 | 1.5 | 3.2 | 7.2 |
|  | 40° C. for 48-72 h (with agitation) | 0.6 | 1.5 | 3.2 | 2.3 |
|  | 40° C. for 72 h (with agitation) | 0.6 | 1.4 | 2.9 | 1.1 |
| Experiment 2 | Control (untreated) | 0.6 | 1.7 | 5.0 | 2.3 |
|  | 40° C. for 48-72 h | 0.7 | 2.0 | 4.7 | 1.1 |

TABLE 1-continued

Conditioning studies, untreated versus treated.

| Conditions | Particle size distribution (μm) by Malvern | | | Amorphous content (%) |
|---|---|---|---|---|
| | D10 | D50 | D90 | |
| (with agitation) | | | | |

Results show amorphous fluticasone propionate particles are conditioned to a more stable low-energy crystalline state in a suspension of HFA134a at 40° C. for 48-72 hrs. The conditioning process is amenable to a range of particle size distributions. The conditioned fluticasone propionate particles are utilised in the manufacturing process to stabilise the pharmaceutical product during long-term storage. Reduction or removal of amorphous content via the process of the present invention is beneficial as the formation of degradation products is minimised and consistent pharmaceutical performance of the stored product is achieved. Further benefits of the present invention are that conditioning is achieved without affecting PSD. This provides improved stability of the API as measured by Aerodynamic Particle Size Distribution (APSD). This also provides improved chemical stability.

Figure 2:
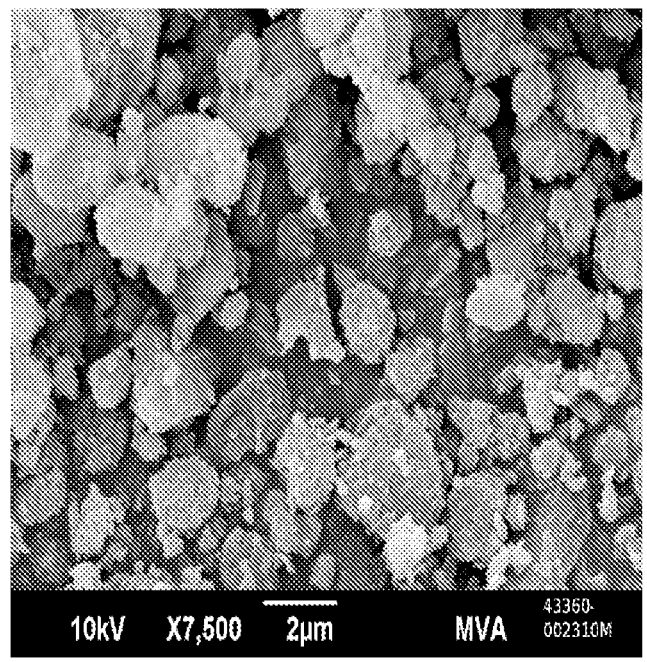
Figure 2:
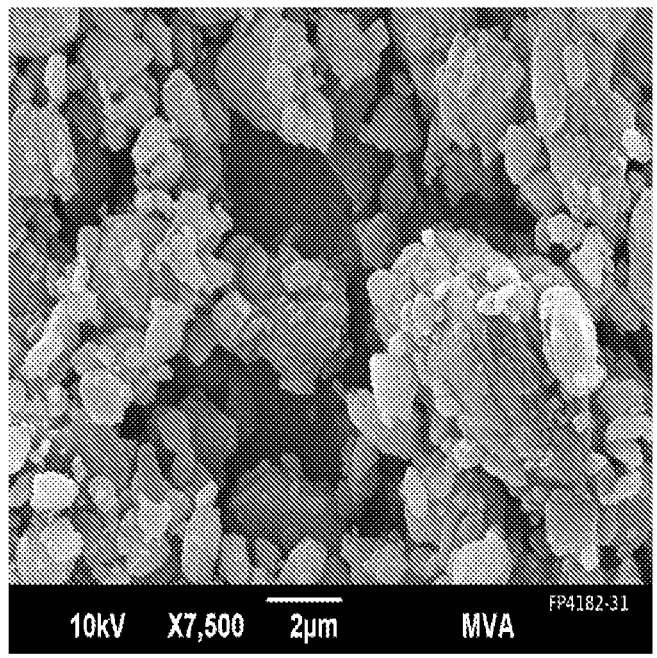

FIGS. 1 and 2 are taken from Experiments 1 and 2 in Table 1 and show scanning electron microscopic images of fluticasone propionate, pre-conditioning (the first image in each Figure) and post-conditioning (the second image in each Figure). The images demonstrate that the API has increased crystallinity (i.e., decreased amorphous content) as a result of being conditioned in accordance with the present invention.

The invention claimed is:

1. A process for preparing an inhalable active pharmaceutical ingredient comprising the steps of:
   simultaneously heating and agitating a suspension of an active pharmaceutical ingredient in a liquefied propellant in a vessel, wherein the heating is performed at a temperature of 30-50° C. for 6 hours to 5 days,
   evaporating the propellant, and
   collecting the resultant powder,
      wherein the active pharmaceutical ingredient has a first amorphous content prior to the simultaneous heating and agitating step, and the resultant powder comprises the active pharmaceutical ingredient having a second amorphous content that is lower than the first amorphous content, and
      wherein the inhalable active pharmaceutical ingredient is one or more of fluticasone proprionate, fluticasone furoate, budesonide, beclomethasone diproprionate, and mometasone furoate.

2. The process as claimed in claim 1, wherein the propellant is a hydrofluoroalkane (HFA) propellant.

3. The process as claimed in claim 2, wherein the propellant is HFA134a or HFA227.

4. The process as claimed in claim 1, wherein the heating is performed at a temperature of 35-45° C.

5. The process as claimed in claim 4, wherein the heating is performed at a temperature of 38-42° C.

6. The process as claimed in claim 1, wherein the heating is performed for 24-84 hours.

7. The process as claimed in claim 1, wherein the heating is performed for 48-72 hours.

8. The process as claimed in claim 1, wherein the inhalable active pharmaceutical ingredient further includes, a $\beta_2$-agonist, an anticholinergic agent, or a combination thereof.

9. The process as claimed in claim 1, wherein the inhalable active pharmaceutical ingredient has a mass median aerodynamic diameter of 1-5 μm.

10. The process as claimed in claim 9, wherein the inhalable active pharmaceutical ingredient is fluticasone propionate or fluticasone furoate.

11. The process as claimed in claim 1, wherein the suspension contains 1-30% active pharmaceutical ingredient based on the combined weight of the active pharmaceutical ingredient and the propellant.

12. A process for preparing an inhalable active pharmaceutical ingredient comprising the steps of:
   simultaneously heating and agitating a suspension of an active pharmaceutical ingredient in a liquefied propellant in a vessel,
   evaporating the propellant, and
   collecting the resultant powder,
      wherein the simultaneous heating and agitating step is performed at a temperature of 30-50° C. for 6 hours to 5 days, and
      wherein the inhalable active pharmaceutical ingredient is one or more of fluticasone propionate, fluticasone furoate, budesonide, beclomethasone diproprionate, and mometasone furoate.

13. The process as claimed in claim 1, further comprising:
   adding the resultant powder comprising the active pharmaceutical ingredient to water to form a nebulisable formulation.

14. The process as claimed in claim 13, further comprising:
   adding, to the nebulisable formulation, at least one of a co-solvent and an acid.

* * * * *